(12) United States Patent
Tanaka

(10) Patent No.: US 9,528,924 B2
(45) Date of Patent: Dec. 27, 2016

(54) PHOTODETECTION DEVICE

(71) Applicant: Sharp Kabushiki Kaisha, Osaka-shi, Osaka (JP)

(72) Inventor: Masaki Tanaka, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 0 days.

(21) Appl. No.: 14/766,801

(22) PCT Filed: Aug. 20, 2014

(86) PCT No.: PCT/JP2014/071753
§ 371 (c)(1),
(2) Date: Aug. 10, 2015

(87) PCT Pub. No.: WO2015/025880
PCT Pub. Date: Feb. 26, 2015

(65) Prior Publication Data
US 2016/0003727 A1 Jan. 7, 2016

(30) Foreign Application Priority Data

Aug. 23, 2013 (JP) ................. 2013-173772

(51) Int. Cl.
*G01N 15/14* (2006.01)
*G01N 21/47* (2006.01)
(Continued)

(52) U.S. Cl.
CPC .......... *G01N 15/14* (2013.01); *G01N 15/0211* (2013.01); *G01N 15/1429* (2013.01);
(Continued)

(58) Field of Classification Search
CPC G01N 15/14; G01N 15/0211; G01N 15/1429; G01N 15/1434; G01N 21/4788; G01N 21/64
See application file for complete search history.

(56) References Cited

U.S. PATENT DOCUMENTS 4,898,471 A 2/1990 Vaught et al.
5,751,839 A 5/1998 Drocourt et al.
(Continued)

FOREIGN PATENT DOCUMENTS

JP 10-3134 A 1/1998
JP 2003-248007 A 9/2003
(Continued)

OTHER PUBLICATIONS

Official Communication issued in International Patent Application No. PCT/JP2014/071753, mailed on Nov. 18, 2014.

*Primary Examiner* — David Porta
*Assistant Examiner* — Mindy Vu
(74) *Attorney, Agent, or Firm* — Keating & Bennett, LLP

(57) ABSTRACT

A photodetection device has an optical module (4) that includes a light source (7), an excitation optical system, and a detection optical system and that two-dimensionally and relatively scans a transparent stage (5) in a first sampling direction and a second sampling direction intersecting the first sampling direction. A scan length in the first sampling direction is longer than a scan length in the second sampling direction. A data sampling unit in the detection optical system performs sampling for a distance of a second sampling interval during scanning in the second sampling direction, and performs sampling for a distance of a first sampling interval shorter than the distance of the second sampling interval during scanning in the first sampling direction. An aperture (10) of the excitation optical system sets a size in the first sampling direction of a spot shape of excitation light from the light source (7) to be smaller than a size in the second sampling direction.

5 Claims, 8 Drawing Sheets

(51) Int. Cl.
  *G01N 15/02*  (2006.01)
  *G01N 21/64*  (2006.01)
  *G01N 15/00*  (2006.01)

(52) U.S. Cl.
  CPC ..... *G01N 15/1434* (2013.01); *G01N 21/4788* (2013.01); *G01N 21/64* (2013.01); *G01N 2015/0065* (2013.01); *G01N 2015/1486* (2013.01)

(56) References Cited

U.S. PATENT DOCUMENTS

| | | |
|---|---|---|
| 5,900,640 A | 5/1999 | Ogura |
| 7,595,874 B1 | 9/2009 | Pelekhaty et al. |
| 2012/0314211 A1* | 12/2012 | Ando ............... G01N 21/47 356/237.2 |

FOREIGN PATENT DOCUMENTS

| | | |
|---|---|---|
| JP | 2003-527558 A | 9/2003 |
| JP | 3928846 B2 | 6/2007 |
| WO | 99/54710 A1 | 10/1999 |

* cited by examiner

PHOTODETECTION DEVICE

TECHNICAL FIELD

The present invention relates to a photodetection device.

BACKGROUND ART

There has hitherto been a microparticle detection device that counts microparticles developed in liquid or on a membrane or a slide glass or conducts a property inspection on the microparticles by irradiating the microparticles with light and detecting fluorescence or scattered light generated from the microparticles. Here, the microparticles include inorganic particles, microorganisms, cells, red blood cells, white blood cells, and platelets in the blood, endothelial cells, small cell debris of the above tissues, and microparticles in the blood. When the microparticles are present in the liquid, they serve as a microparticle suspension.

A flow cytometer is popular as a detection method for the microparticles. In this flow cytometer, a suspension of the microparticles is run through a capillary together with sheath fluid. A part of the capillary is irradiated with laser light, and the kind of the microparticles and the size of the microparticles are sorted by detecting scattered light or fluorescence generated when the microparticles are irradiated with the light. For example, by labeling particles with a fluorescent reagent that bonds to specific particles, the number of fluorescence-emitting particles can be counted and only the specific particles can be counted. This flow cytometer can detect particles from the submicron order to about 10 µm, and can achieve high-accuracy detection.

However, the above-described flow cytometer that can measure even particles of the submicron order is a large-sized and expensive system.

In contrast, there is a particle detection method that measures an image of particles and identifies the kind and size of the particles from information about the image. Since this method performs detection and analysis of the particles by using the image, it is sometimes called an image cytometer in contrast to the flow cytometer. Imaging methods include photographing using a microscope and a digital camera and a method that performs imaging by detecting scattered light or fluorescence while two-dimensionally scanning an optical head.

In the case of photographing using the microscope and the digital camera, when particles have a size of 1 µm or more, a high-accuracy image can be measured. However, when particles of the submicron order are measured, a microscope having a high-power objective lens and a highly sensitive (that is, low-noise and wide dynamic range) digital camera are necessary. Hence, the system is considerably expensive. In the case of submicron particles, since the light wavelength and the particle size are equal, imaging performance is reduced by the diffraction limit, and it is difficult to exactly identify the particle size.

Further, particles can be easily detected by using a fluorescence microscope system as the above microscope. However, similarly, the light wavelength and the particle size are equal to each other when the particles are submicron particles. Hence, the particle size cannot be identified exactly. Further, since fluorescence from the microparticles is faint, a highly sensitive digital camera is necessary.

In contrast to this, in the system that detects scattered light or fluorescence while scanning the optical head, laser light from the optical head is collected and applied to particles, and the optical head is two-dimensionally scanned to perform imaging while detecting scattered light or fluorescence generated from the particles.

As such a system that detects light while scanning the optical head, Japanese Patent No. 3928846 (PTL 1) discloses a scanner having a confocal optical system.

In the scanner having the confocal optical system disclosed in PTL 1, laser light emitted from a laser excitation light source is turned into parallel light by a collimator lens, passes through a hole of a holed mirror and a first lens in an optical head, and enters a sample set on a sample stage that is movable in the X-direction and the Y-direction. When the sample is a fluorescence sample, a fluorescent substance is excited by the laser light and fluorescence is emitted. When the sample is a storage phosphor sheet, a stimulable phosphor is excited by the laser light, and stimulable light is emitted. The light thus emitted from the sample is turned into parallel light by the first lens, is reflected by a portion around the hole of the holed mirror, and is collected by a second lens. Then, the light passes through a confocal switch member disposed at the focal position of the second lens, and is photoelectrically detected by a photomultiplier, so that analog data is generated.

In the system that thus detects light while scanning the optical head relative to the sample, when submicron particles are detected, the irradiation spot diameter of the laser light is equal to or larger than the particle size. For this reason, individual particles are not resolved in an image obtained as a result of two-dimensional scanning. Hence, it is difficult to directly measure the size of the particles from the image. However, even when the irradiation spot size of the laser light is larger than the particle size, the intensity of scattered light generated from the particles differs according to the particle size. Hence, it is possible to identify the particle size from the intensity of scattered light. This is because the particle size and the intensity of scattered light are correlated with each other.

In this case, although a detector for detecting scattered light with high sensitivity (a low-noise and wide dynamic range detector) and a laser light source are necessary, it is possible to configure a system that is less expensive than the system using the microscope having the high-power objective lens and the highly sensitive digital camera.

However, the above-described conventional system, which detects light while scanning the optical head relative to the sample, has the following problems.

That is, in the above system that detects scattered light from the sample by two-dimensional scanning, measurement needs to be performed while decreasing the scan pitch of the two-dimensional scanning as the particle size decreases. This is because particles may be skipped when the scan pitch is larger than the particle diameter. However, a new problem occurs, that is, the measurement time increases as the measurement pitch (scan pitch) decreases.

When the irradiation spot diameter of laser light is set to be larger than the particle size, the particles are not skipped. However, the intensity of scattered light decreases and the particle size may be misread.

However, the scanner having the confocal optical system disclosed in PTL 1 is a typical fluorescent imaging system, but is not intended to detect microparticles. Therefore, PTL 1 does not describe the problem caused when the scan pitch is decreased because the particle size is small and the problem caused when the irradiation spot diameter of laser light is increased.

CITATION LIST

Patent Literature

PTL 1: Japanese Patent No. 3928846

SUMMARY OF INVENTION

Technical Problem

Accordingly, an object of the present invention is to provide a photodetection device that can detect the intensity of scattered light from particles at high speed and with high accuracy without skipping the particles.

Solution to Problem

To solve the above problems, a photodetection device according to the present invention includes:

a light-transmitting transparent stage on which a detection object is placed;

an excitation optical system that irradiates the detection object with excitation light emitted from a light source;

a detection optical system that detects light emitted from a detection surface of the detection object placed on the transparent stage by irradiation with the excitation light;

a data sampling unit included in the detection optical system to sample an intensity of the detected light at a predetermined set interval; and an optical module that includes the light source, the excitation optical system, and the detection optical system and that two-dimensionally and relatively scans the transparent stage in a first sampling direction of the data sampling unit and a second sampling direction intersecting the first sampling direction, wherein a scan length in the first sampling direction in the optical module is longer than a scan length in the second sampling direction, wherein the data sampling unit performs the sampling at a first sampling interval when the optical module performs scanning in the first sampling direction, and performs the sampling at a second sampling interval different from the first sampling interval when the optical module performs scanning in the second sampling direction, wherein the excitation optical system includes an aperture that sets a spot shape of the excitation light to irradiate the detection object, wherein a distance of the first sampling interval is set to be shorter than a distance of the second sampling interval, and wherein the spot shape of the excitation light is set by the aperture so that a spot size in the first sampling direction is smaller than a spot size in the second sampling direction.

In the photodetection device according to an embodiment, a ratio of the distance of the second sampling interval to the distance of the first sampling interval is two or more, and a ratio of the spot size in the second sampling direction to the spot size in the first sampling direction of the spot of the excitation light is two or more.

In the photodetection device according to an embodiment, microparticles that emit light by irradiation with the excitation light are two-dimensionally dispersed in the detection object, a size of the microparticles is smaller than the spot size in the first sampling direction of the spot of the excitation light formed on the detection object, and the detection optical system detects the microparticles dispersed in the detection object by detecting the light emitted from the microparticles.

The photodetection device according to an embodiment includes:

a first operating unit that causes the optical module to reciprocate relative to the transparent stage in the first sampling direction, and a second operating unit that causes the optical module to reciprocate relative to the transparent stage in the second sampling direction substantially orthogonal to the first sampling direction.

In the photodetection device according to an embodiment, the first sampling direction is a direction of a circumference, and the second sampling direction is a radial direction of the circumference, and the photodetection device includes a first operating unit that causes the transparent stage to rotate on a center of the circumference relative to the optical module; and a second operating unit that causes the optical module to reciprocate relative to the transparent stage in the second sampling direction.

Advantageous Effects of Invention

As is clear from the above, in the photodetection device of the present invention, the distance of the first sampling interval in the first sampling direction that can be shortened because the first sampling direction is a long scanning direction is set to be shorter than the distance of the second sampling interval in the second sampling direction that cannot be shortened because the second sampling direction is a short scanning direction. Thus, it is possible to allow sampling for obtaining the detection light intensity at high speed and with high accuracy as a whole.

Further, the shape of the spot of the excitation light from the light source on the detection object is set so that the spot size in the first sampling direction is smaller than the spot size in the second sampling direction. That is, the size is set to be small in the direction in which the sampling interval is short and the size is set to be large in the direction in which the sampling interval is long. In this way, it is possible to reduce the increase of skipping of light from the microparticles and the like emitted from the detection surface of the detection object owing to the inability to shorten the distance of the second sampling interval in the second sampling direction serving as the short scanning direction, to increase the detection speed for light emitted from the detection surface during scanning in both of the directions, and to further increase the detection accuracy.

DESCRIPTION OF EMBODIMENTS

The present invention will be described in detail below in conjunction with illustrated embodiments.

First Embodiment

Figure 1:
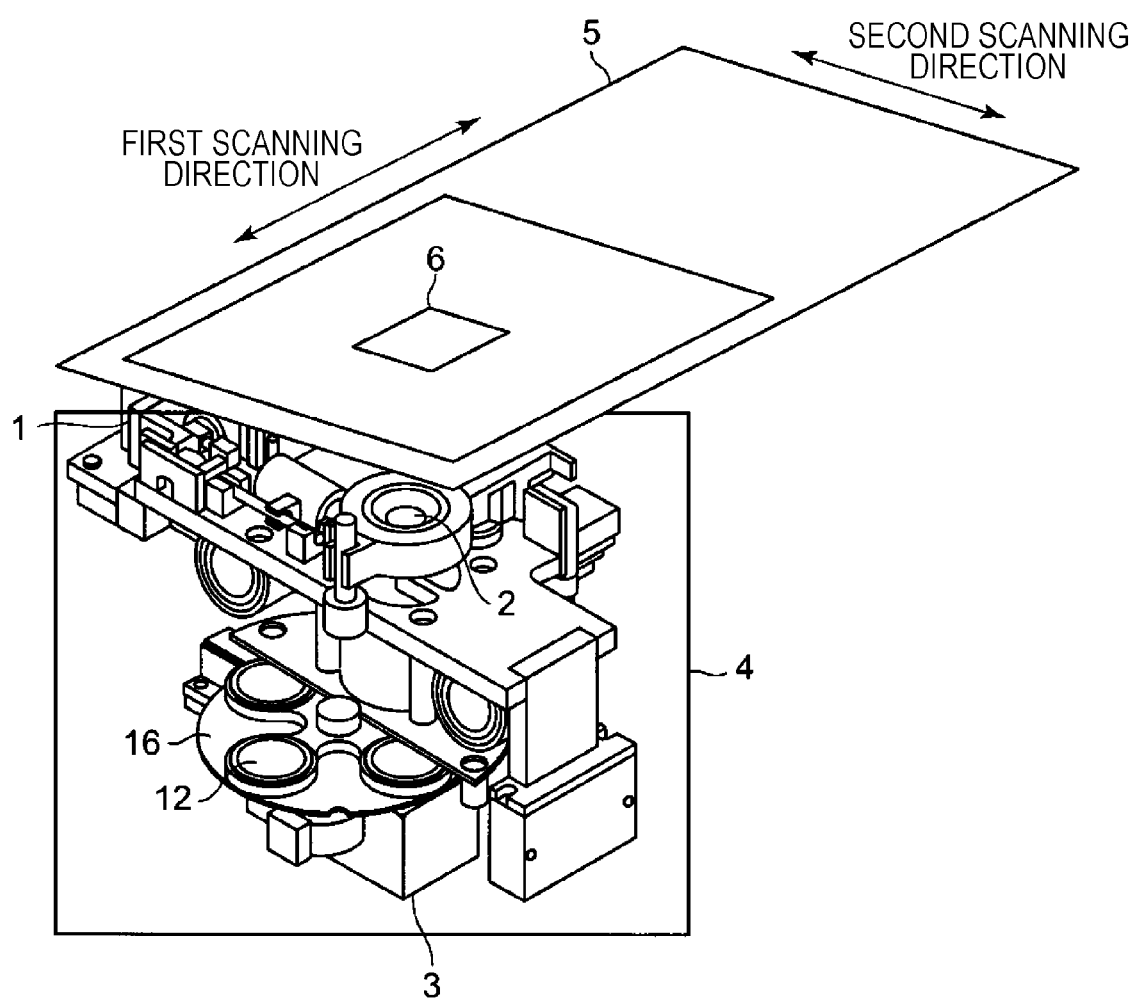
FIG. 1 is a perspective view of a photodetection device according to the present invention.
Figure 2:
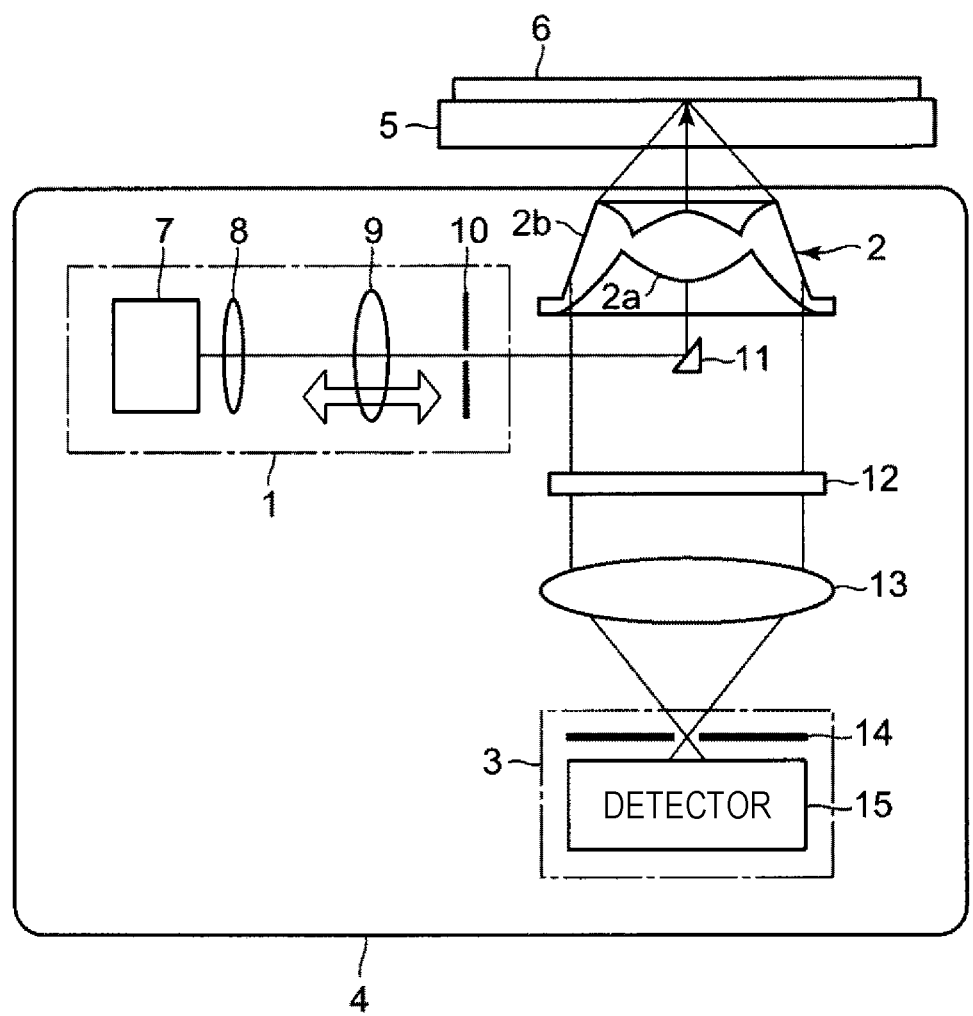
FIG. 2 is a schematic cross-sectional view of an optical module in FIG. 1.

FIGS. 1 and 2 illustrate a schematic configuration of a photodetection device according to this embodiment. FIG. 1 is an overall perspective view, and FIG. 2 is a schematic cross-sectional view of an optical module.

In FIG. 1, reference numerals 1, 2, and 3 denote a light source device, an objective lens, and a detection device, respectively. The light source device 1, the objective lens 2, and the detection device 3 are housed in a frame to constitute the optical module 4. Above the optical module 4, a glass stage 5 serving as the transparent stage is disposed to be opposed to the objective lens 2. On the glass stage 5, for example, a suspension, a gel support, or a transfer support, such as a membrane, in which microparticles labeled with a fluorescent substance are distributed is set as a sample (detection object) 6.

Here, the glass stage 5 is rectangular, and is configured to be scanned in two-dimensional directions, that is, a first scanning direction serving as a longer side direction and a second scanning direction serving as a shorter side direction orthogonal to the first scanning direction. The scanning method in this case is not particularly limited. In short, it is only necessary to provide a first operating unit that causes the glass stage 5 to reciprocate in the first direction and a second operating unit that causes the glass stage 5 to reciprocate in the second scanning direction. Alternatively, the optical module 4 may be scanned in two-dimensional directions.

The light source device 1 in the optical module 4 includes a semiconductor laser 7 serving as a light source. At an intersecting position of the optical axis of the objective lens 2 and the optical axis of the semiconductor laser 7, a prism 11 is disposed to reflect laser light emitted from the semiconductor laser 7 and collected by a first lens 8, a spot-size adjusting lens 9, and an aperture 10 so that the laser light is incident on the objective lens 2. The semiconductor laser 7, the first lens 8, the spot-size adjusting lens 9, the aperture 10, the prism 11, and the objective lens 2 constitute the excitation optical system. Among these, the semiconductor laser 7, the first lens 8, the spot-size adjusting lens 9, and the aperture 10 are housed in one case to constitute the light source device 1.

Although not described in detail here, the objective lens 2 is housed in a lens holder (not illustrated), and is moved in the optical axis direction by a driving unit such as a stepping motor (not illustrated) to change the focal position. Further, the spot-size adjusting lens 9 is housed in a lens holder (not illustrated), and is moved in the optical axis direction by a driving unit (not illustrated) to adjust the spot size.

In FIG. 2, below the prism 11 on the optical axis of the objective lens 2, an ND (neutral density) filter 12 for reducing the intensity of fluorescence from the sample 6, which is collected by the objective lens 2 and turned into parallel light, a second lens 13 for collecting the fluorescence passed through the ND filter 12, and a pinhole 14 for cutting stray light of the fluorescence passed through the second lens 13 are arranged in this order from the side of the prism 11. Further, below the pinhole 14 on the optical axis of the objective lens 2, a detector 15 including a detection element, such as a photomultiplier tube (PMT), which detects the fluorescence passed through the pinhole 14, is disposed. The objective lens 2, the ND filter 12, the second lens 13, the pinhole 14, and the detector 15 constitute the detection optical system. Among these, the pinhole 14 and the detector 15 are housed in one case to constitute the detection device 3.

In the optical module 4 having the above-described configuration, excitation light emitted from the semiconductor laser 7 is converged by the first lens 8, the spot-size adjusting lens 9, and the aperture 10, is next reflected by the prism 11, passes through the objective lens 2 and the glass stage 5, and is collected at one point on a lower surface of the sample 6. In this case, the length of the prism 11 in a longitudinal direction (horizontal direction) is short, and the width of the prism 11 in a direction orthogonal to the longitudinal direction is narrow. The excitation light from the semiconductor laser 7 passes only through a portion of the objective lens 2 near the optical axis (an excitation-light transmitting portion).

The fluorescence is isotropically emitted around from a portion of the sample 6 irradiated with the excitation light. Then, a component of the emitted fluorescence, which passes through the glass stage 5 formed of glass and enters the objective lens 2, passes through the objective lens 2, the ND filter 12, the second lens 13, and the pinhole 14, and is detected by the detector 15. Then, for example, signals detected by the detector 15 are subjected to processing, such as AD conversion, by a built-in AD converter, and is then sent to a PC (personal computer). In this way, a distribution of fluorescence intensities at measuring points on the sample 6 is recorded in, for example, an internal memory.

Hereinafter, light passed through the objective lens 2, of the fluorescence isotropically scattered around from the portion irradiated with the excitation light, as described above, is sometimes simply referred to as scattered light.

As illustrated in FIG. 1, for example, the ND filter 12 for reducing light is disposed in a rotating folder 16, and can be replaced with filters for other light reducing amounts according to the amount of fluorescence. The pinhole 14 has the effect of removing stray light and scattered light from portions other than the detection surface. For example, fluorescence generated on a back surface (upper surface) of the sample 6 becomes light spread at the position of the pinhole 14 by the optical system subsequent to the objective lens 2 because the back surface deviates from the focal position of the objective lens 2. Such stray light cannot efficiently pass through the pinhole, but is removed by the pinhole 14.

As illustrated in FIG. 2, a center portion of the objective lens 2 including the optical axis serves as a convex lens part 2a having the function of a normal convex lens (the function of deflecting light only by refraction). Excitation light emitted from the semiconductor laser 7 and reflected by the prism 11 passes through the convex lens part 2a, and is converged toward the sample 6. A fluorescence component having a small radiation angle, of the fluorescence emitted from the sample 6, passes through the convex lens part 2a, and is collected toward the detector 15.

A portion of the objective lens 2 around the convex lens part 2a serves as a truncated conical cylindrical body 2b opening downward. A fluorescence component having too wide an emission angle to fit in the convex lens part 2a, of the fluorescence emitted from the sample 6, enters the cylindrical body 2b from an upper end surface of the cylindrical body 2b, is deflected toward the optical axis by total reflection on an outer peripheral surface of the cylindrical body 2b, and is emitted from an inner peripheral surface and a lower end surface of the cylindrical body 2b toward the detector 15.

As described above, even light having too wide an emission angle to be collected by the normal convex lens can be collected by totally reflecting, by the outer peripheral surface of the cylindrical body 2b, the fluorescence component having too wide an emission angle to fit in the convex lens part 2a, of the fluorescence emitted from the sample 6. For this reason, sensitivity of the detector 15 can be increased.

Detection of fluorescence (scattered light) isotropically scattered around from the portion of the lower surface of the sample 6, where excitation light is collected, from the side of the sample 6 irradiated with the excitation light, as in this embodiment, is referred to as "backward scattered light detection."

As described above, this embodiment adopts the configuration in which the optical module 4 is fixed and a distribution image of scattered light intensity is read by scanning the glass stage 5 on which the sample 6 is placed in two-dimensional directions.

Figure 3:
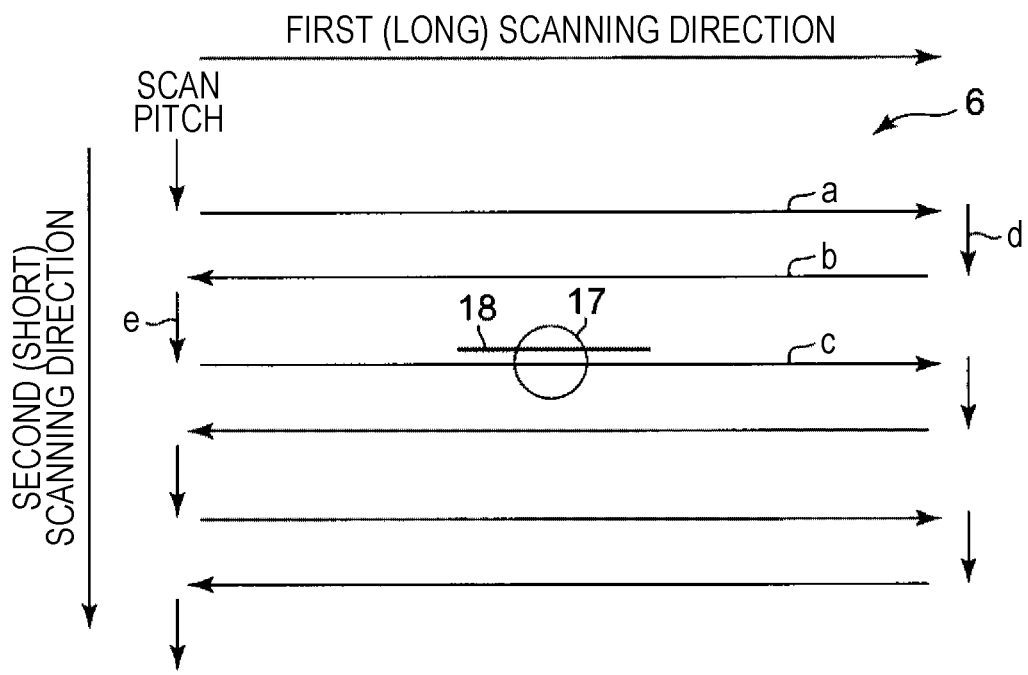
FIG. 3 illustrates a scan trajectory of excitation light drawn on a sample by two-dimensional scanning.

When the glass stage 5 is thus two-dimensionally scanned relative to the optical module 4 alternatively in the first scanning direction (longer side direction) and the second scanning direction (shorter side direction), as illustrated in FIG. 3, a scan trajectory of the light collection point of the excitation light is drawn on the sample 6 by the objective lens 2. The scan trajectory is formed by continuously repeating straight lines a, b, and c that reciprocate in the directions of arrows with spaces therebetween, a straight line d that connects a leading end portion of the straight line a and a root portion of the straight line b in a direction of arrow, and a straight line e that connects a leading end portion of the straight line b and a root portion of the straight line c in a direction of arrow.

Figure 4:
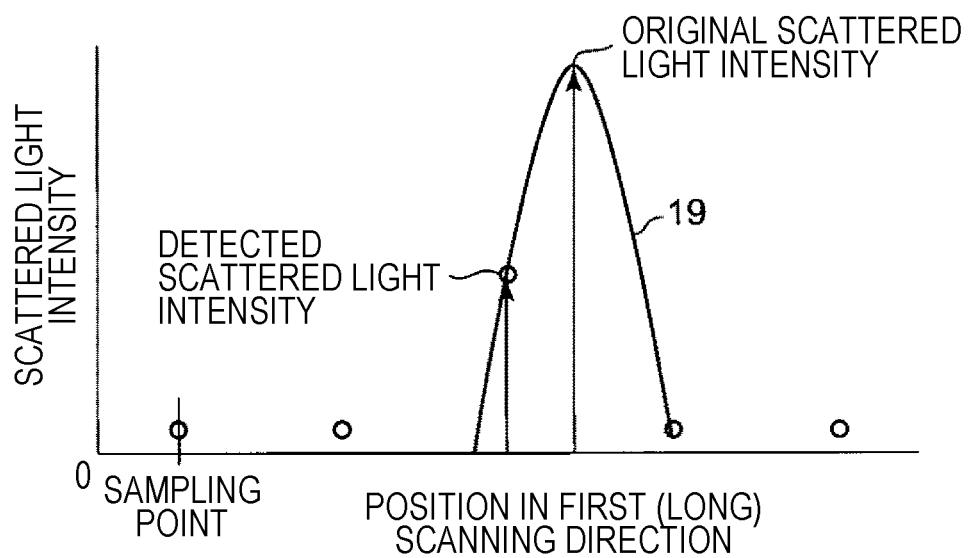
FIG. 4 shows detection data near microparticles obtained by two-dimensional scanning of FIG. 3.

When two-dimensional scanning is thus performed over the sample 6, in a case in which a microparticle 17 is located at a position of the scan trajectory of the straight line c, analog data (original scattered light intensity) is detected by the detector 15 during scanning of an area 18 on the straight scan trajectory c, as shown by a curve 19 in FIG. 4. However, as described above, AD conversion is performed by the AD converter or the like serving as the built-in data sampling unit in the detector 15. Therefore, detection data (detected scattered light intensity) input from the detector 15 to the PC is a discrete value shown by a circle on the curve 19 in FIG. 4. In this case, since the data acquisition interval (distance of the sampling interval) of the AD converter is substantially equal to the diameter of the microparticle 17, a data acquisition point (measuring point) sometimes deviates from the peak of the curve 19. In this case, the digital detection value of the detector 15 cannot represent original scattered light intensity.

In this case, there are few problems when the presence of particles, that is, the number and positions of particles are measured by the digital scattered light intensity. However, when the particle diameter is measured by the digital scattered light intensity, inaccuracy of the digital scattered light intensity directly leads to inaccuracy of the particle diameter, and this causes a serious problem.

Figure 5:
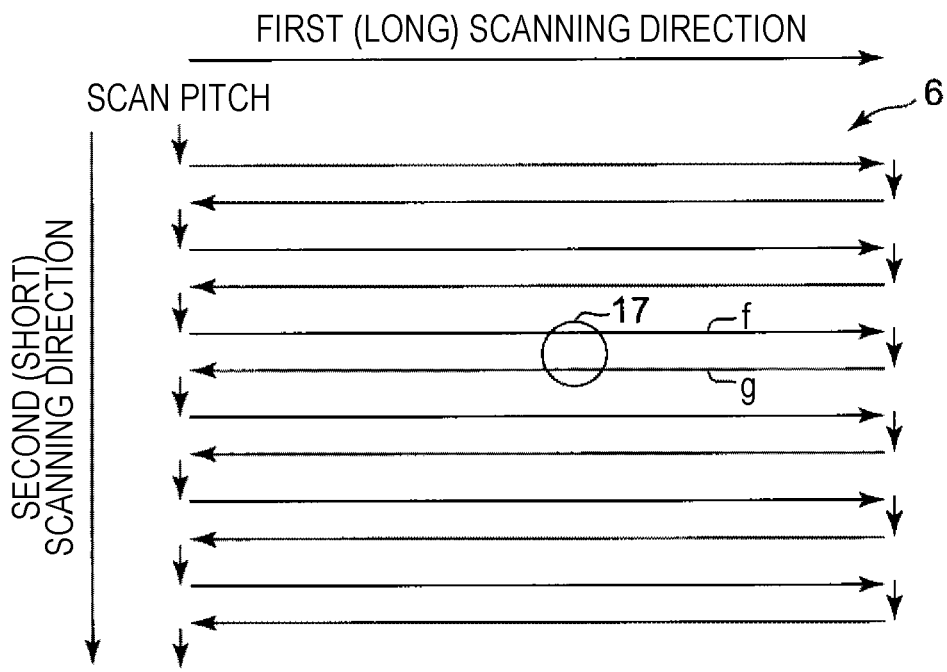
FIG. 5 illustrates a scanning trajectory when the scan pitch in a second scanning direction is decreased from the state of FIG. 3.

FIG. 5 shows a scan trajectory in a state in which the scan pitch in the second scanning direction is decreased from the state of FIG. 3. In this case, since the scan pitch in the second scanning direction is decreased, the microparticle 17 can be scanned twice along a straight scan trajectory f and a straight scan trajectory g in the first scanning direction, and this increases the image accuracy. For this reason, when the particle diameter is measured by the digital scattered light intensity, the possibility of misreading the particle diameter can be reduced.

However, scanning takes much time because the scan number in the second scanning direction increases.

Figure 6:
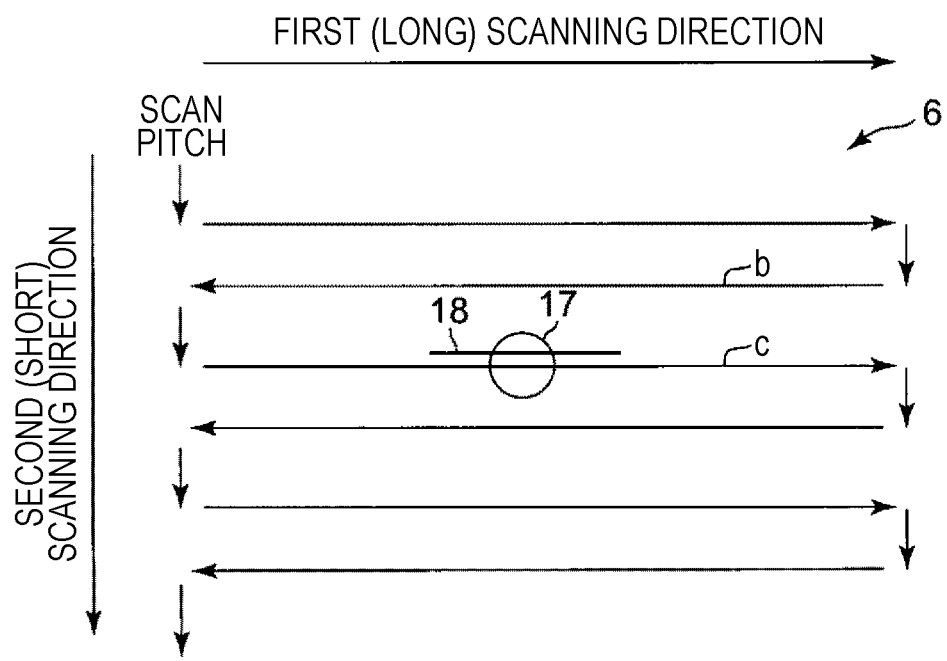
FIG. 6 illustrates a scanning trajectory when the data sampling interval in a first scanning direction is decreased from the state of FIG. 3.
Figure 7:
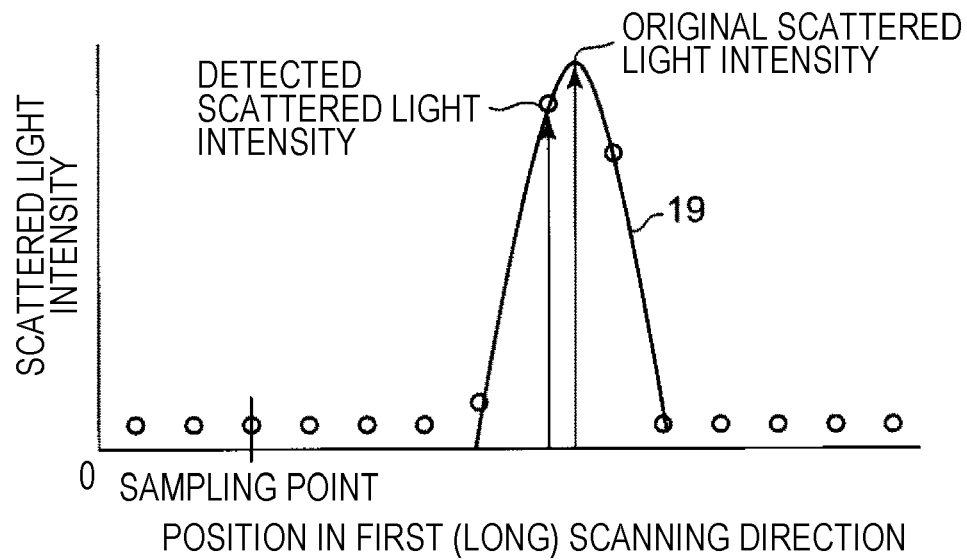
FIG. 7 shows detection data near microparticles obtained by two-dimensional scanning of FIG. 6.

FIG. 6 shows a scan trajectory in a state in which the data sampling interval of the AD converter during scanning in the first scanning direction is decreased from the state of FIG. 3. The scan trajectory in this case is the same as the scan trajectory in FIG. 3. However, the number of detection data (scattered light intensities) from the detector 15 shown by circles on a curve 19 in FIG. 7 is increased because the sampling interval of the AD converter is decreased. For this reason, "detected scattered light intensity" based on the measured values shown by the circles is substantially close to "original scattered light intensity" based on analog measured values shown by the curve 19. This allows more accurate measurement than in FIG. 3.

In this case, since a raw data image obtained by the PC is an image expanded in the first scanning direction by the increase ratio of the data acquisition interval per unit time in FIG. 6 to the data acquisition interval per unit time in FIG. 3 because the data sampling interval of the AD conversion in the detector 15 is expressed as the same length on the image. Accordingly, the PC needs to make correction to shorten the length in the first scanning direction by the increase ratio.

The intensity of fluorescence from the microparticle 17 in the sample 6 mainly depends on how excitation light impinges on the microparticle 17. To increase the intensity of fluorescence scattered from the microparticle 17, the excitation light needs to be narrowed into a small spot so that strong excitation light is applied to a narrow area. Further, scanning in the second scanning direction is performed while shifting the excitation light little by little so that adjacent areas of the excitation light overlap with each other.

At this time, the reason why the intensity of fluorescence from the microparticle 17 varies is that there is an intensity distribution in the spot area of excitation light and that, if the microparticle 17 is not located at the center of the spot where the light intensity is the highest, the intensity of fluorescence decreases and the microparticle 17 cannot be properly caught. To solve the problem of variation of fluorescence from the microparticle 17, the opportunity to locate the microparticle 17 at almost the center of the excitation light spot needs to be increased by shortening the sampling interval of the detector 15.

Here, the sampling interval in the first scanning direction can be set by the circuit configuration of the AD converter in the detector 15. In contrast, the sampling interval in the second scanning direction is set by movement of the glass stage 5 in the second scanning direction. In this case, the moving interval (scan pitch) of the glass stage 5 in the second scanning direction cannot be easily changed because there is a relation with the moving mechanism for the glass stage 5. In contrast, the interval of AD conversion in the detector 15 can be set by the circuit configuration and a driving program of the AD converter, and this setting is relatively easy.

From another standpoint, when a planar stage like the glass stage 5 is two-dimensionally scanned, the scanning direction is divided into a long scanning direction in the longer side direction like the first scanning direction and a short scanning direction in the shorter side direction like the second scanning direction. In scanning in the long scanning direction, since the scan distance in one scanning operation is long, scanning can be easily and continuously performed for a long distance at high speed and at a short sampling interval. In contrast to this, in scanning in the short scanning direction, since the scan distance in one scanning operation is short, the above-described high-speed scanning is difficult.

Accordingly, in this embodiment, since the sampling interval can be more easily shortened in the first scanning direction serving as the long scanning direction, the distance (scan pitch) of the second sampling interval in the second scanning direction (short scanning direction) is set at a length that can obtain the minimum required resolution, and the distance of the first sampling interval in the first scanning direction (long scanning direction) is made shorter than the distance of the second sampling interval. This allows high-speed sampling that obtains a high-accuracy scattered-light intensity image as a whole.

However, even by doing only this, skipping of the microparticle 17 in the second scanning direction (short scanning direction) cannot be suppressed. Accordingly, for this problem, the spot size of excitation light from the semiconductor laser 7 that irradiates the lower surface of the sample 6 is set so that the length in the second scanning direction is longer than the length in the first scanning direction.

Figure 8:
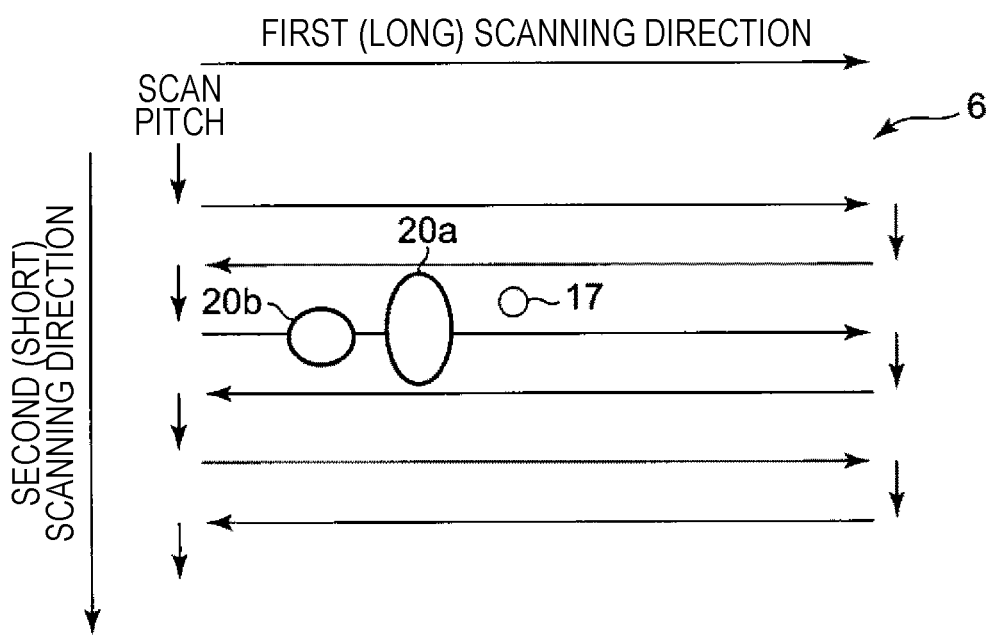
FIG. 8 illustrates spots of excitation light from a semiconductor laser on the sample.

The shape of the spot of excitation light from the semiconductor laser 7 is set by the aperture 10 subsequent to the spot-size adjusting lens 9 in the light source device 1. A light transmission hole provided in the aperture 10 is shaped like an ellipse whose long axis direction is the shorter side direction of the glass stage 5, that is, the longitudinal direction of the prism 11. FIG. 8 illustrates spots of excitation light provided on the same scan trajectory as that of FIG. 6. A spot 20a corresponds to a case in which the aperture 10 is used, and is shaped like an ellipse whose length in the second scanning direction is longer than in the first scanning direction. A spot 20b corresponds to a case in which the aperture 10 is not used, and is shaped like a circle.

In this way, when the spot on the sample 6 of excitation light from the semiconductor laser 7 is shaped like an ellipse whose length in the second scanning direction (short scanning direction) is longer than the length in the first scanning direction (long scanning direction), even if there is a particle whose center position somewhat deviates from the straight scan trajectory in the second scanning direction, the particle is irradiated with the excitation light. Hence, the decrease in detection accuracy of scattered light from the microparticle 17 can be suppressed. Therefore, it is possible to suppress skipping of the microparticle 17 in the second scanning direction due to the sampling interval in the second scanning direction (short scanning direction) having the length that can obtain the minimum required resolution.

That is, according to this embodiment, the sampling interval is decreased in the first scanning direction (long scanning direction), and the size of the excitation light spot is increased in the second scanning direction (short scanning direction). This can increase the detection speed of scattered light from the microparticle 17 during scanning in both of the directions, and can increase the detection accuracy. Therefore, the particle is not skipped, and accurate scattered light intensity can be measured at high speed.

Incidentally, when the size of the spot of the excitation light is increased in both of the first scanning direction (long scanning direction) and the second scanning direction (short scanning direction), the total spot size becomes too large. As a result, the intensity of the excitation light is decreased, and the scattered light intensity is decreased. This makes the measurement value of the particle diameter inaccurate.

During scanning in the second scanning direction (short scanning direction), sampling is performed by the AD converter every time the glass stage 5 is relatively moved in the second scanning direction by the scan pitch, but is not performed during the movement. Therefore, it is possible to say that the scan pitch in the second scanning direction (short scanning direction) is the sampling interval in the second scanning direction.

Accordingly, in this embodiment, it is preferable to set the ratio of the second sampling interval (distance) in the second scanning direction (short scanning direction) to the first sampling interval (distance) in the first scanning direction (long scanning direction) at two or more, and to set the ratio of the size of the spot of excitation light on the sample 6 in the second scanning direction to the size in the first scanning direction at two or more. This is because the effects of increasing the detection speed of scattered light from the microparticle 17 and increasing the detection accuracy can be clearly obtained.

The sample 6 serving as the detection object is a suspension, a gel support, or a transfer support in which microparticles 17 for scattering fluorescence by the irradiation with light from the semiconductor laser 7 serving as the light source are two-dimensionally dispersed. It is preferable that the size of the microparticles 17 should be smaller than the size of the spot of the excitation light on the sample 6 in the first scanning direction (long scanning direction) because this can prevent the microparticles 17 from being skipped in the first scanning direction (long scanning direction).

Second Embodiment

When the microparticles are irradiated with laser light, scattered light occurs, as in the above-described flow cytometer. Of the scattered light, forward scattered light that scatters at a low angle to the traveling direction of the laser light represents the size of the microparticles because the intensity thereof is proportional to the surface are of the microparticles. Hence, the forward scattered light is used to measure the size of the microparticles.

In this embodiment, the particle diameter is measured using the forward scattered light.

Figure 9:
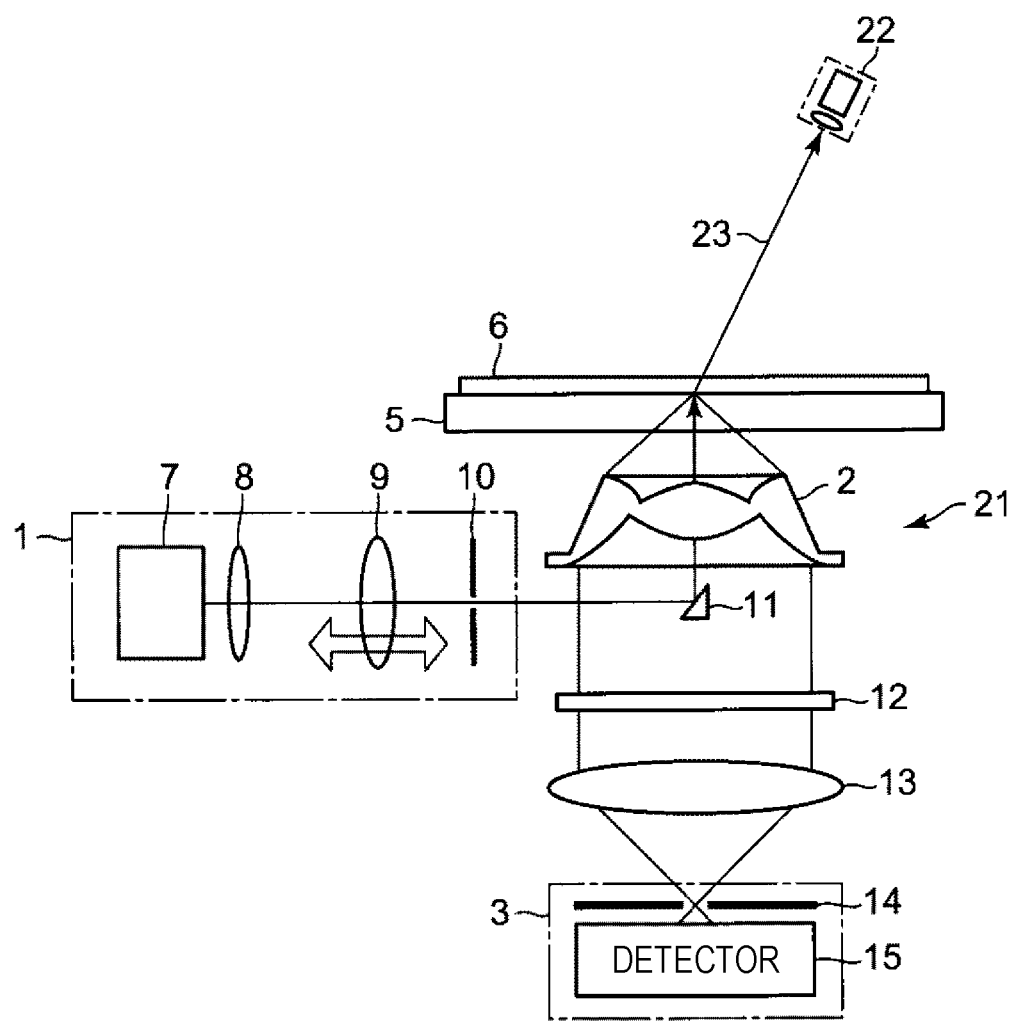
FIG. 9 is a schematic cross-sectional view of an optical module different from the optical module of FIG. 2.

FIG. 9 illustrates the schematic configuration of an optical module in a photodetection device according to this embodiment. An optical module 21 illustrated in FIG. 9 has a configuration substantially equal to that of the optical module 4 of the first embodiment illustrated in FIG. 2. The same members as those adopted in the optical module 4 of FIG. 2 are denoted by the same reference numerals, and detailed descriptions thereof are skipped.

In FIG. 9, on a side of a sample 6 opposite from the optical module 21 and at a position slightly apart from the optical axis of an objective lens 2 and at a distance from the sample 6, a detector 22 is disposed to detect forward scattered light that scatters in the traveling direction of excitation light (laser light), which is emitted from a semiconductor laser 7 and converged by a convex lens part 2a of the objective lens 2, at a low angle to the traveling direction of the excitation light. Hereinafter, this detector 22 is referred to as a second detector 22, and the above-described detector 15 including a PMT is referred to as a first detector 15. The second detector 22 is composed of a photodiode and a low-noise amplifier.

Detecting fluorescence, which is isotropically scattered around from a portion of a lower surface of the sample 6 where the excitation light is collected, from the side of the sample 6 opposite from the side irradiated with the excitation light, as in this embodiment, is referred to as "forward scattered light detection."

In the above configuration, the excitation light emitted from the semiconductor laser 7 is converged by a first lens 8, a spot-size adjusting lens 9, and an aperture 10, is next reflected by a prism 11, passes through the convex lens part 2a of the objective lens 2 and a glass stage 5, and is then collected at one point on the lower surface of the sample 6.

Of the fluorescence isotropically emitted around from the portion of the lower surface of the sample 6 irradiated with the excitation light, forward scattered light 23 passed through the sample 6 and emitted at the low angle to the optical axis of the objective lens 2 is detected by the second detector 22. Signals detected by the second detector 22 are subjected to AD conversion, and are sent, for example, to the PC (or a PC different from the PC for the first detector 15).

At this time, the glass stage 5 performs two-dimensional scanning, and a distribution of fluorescence intensities at measurement points on the sample 6 is obtained.

In this case, similarly to the above-described first embodiment, sampling for obtaining a high-accuracy scattered light intensity image at high speed as a whole can be performed by setting the distance of the second sampling interval in the second scanning direction (short scanning direction) at a length that can obtain the minimum required resolution and setting the distance of the first sampling interval in the first scanning direction (long scanning direction) to be shorter than the distance of the second sampling interval. Further, skipping of microparticles in the second scanning direction is suppressed by setting the spot size of the excitation light from the semiconductor laser 7 that irradiates the lower surface of the sample 6 by the aperture 10 of the light source device 1 so that the length of the spot size in the second scanning direction is longer than the length in the first scanning direction.

In this way, the detection speed of scattered light from the microparticles during scanning in both of the scanning directions is increased, and the detection accuracy is increased.

Third Embodiment

As described above, the size of the microparticles can be measured by "forward scattered light detection." However, "forward scattered light detection" is less advantageous in terms of sensitivity of the second detector 22 than "backward scattered light detection" in which even light having too wide an emission angle to be collected by the normal convex lens can be collected by the objective lens 2 having the convex lens part 2a and the cylindrical body 2b.

Accordingly, in this embodiment, the "forward scattered light detection" and the "backward scattered light detection" are used together. Forward scattered light that is disadvantageous in terms of sensitivity of the detector is used to detect the kind and position of the microparticles, and backward scattered light that is advantageous in terms of sensitivity of the detector is used to detect the size of the microparticles.

Figure 10:
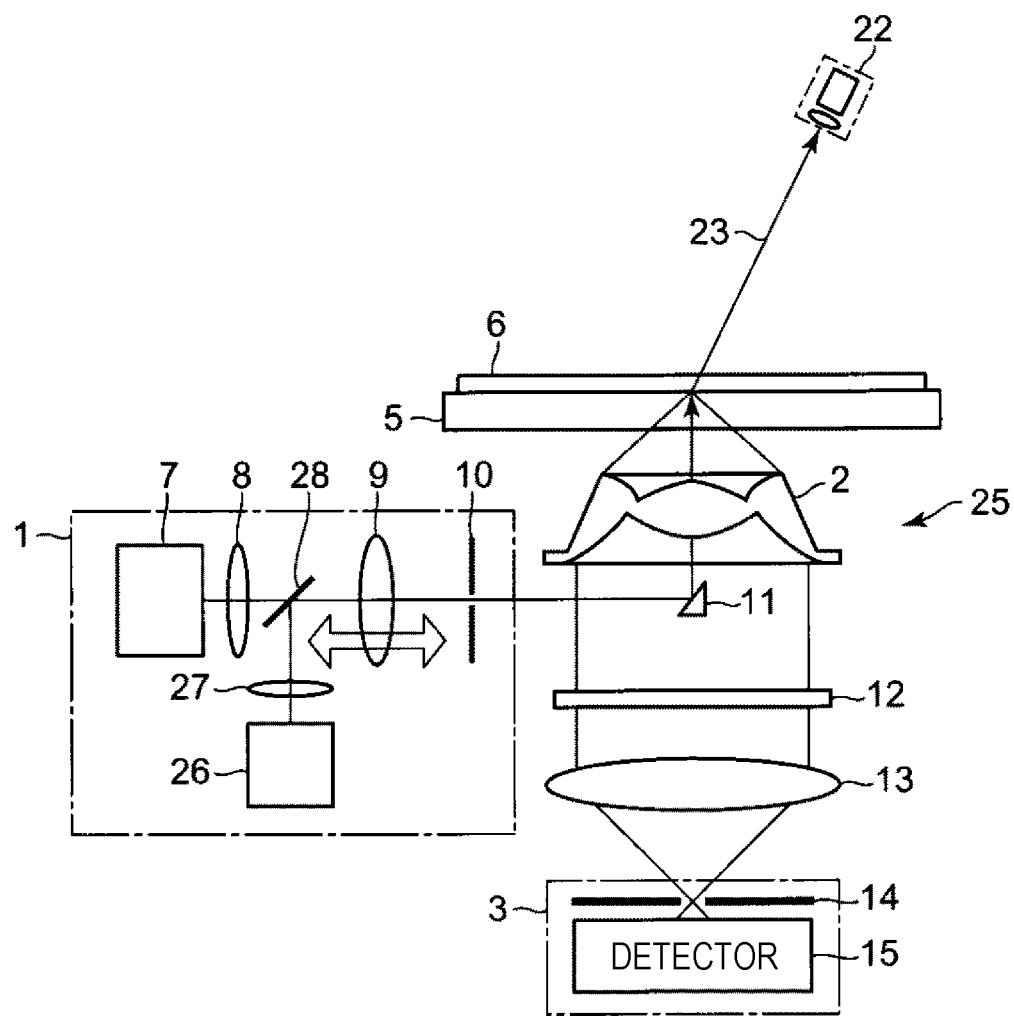
FIG. 10 is a schematic cross-sectional view of an optical module different from the optical modules of FIGS. 2 and 9.

FIG. 10 illustrates the schematic configuration of an optical module in a photodetection device according to this embodiment. An optical module 25 illustrated in FIG. 10 has a configuration substantially equal to those of the optical module 4 of the first embodiment illustrated in FIG. 2 and the optical module 21 of the second embodiment illustrated in FIG. 9. The same members as those in the optical module 4 of FIG. 2 and the optical module 21 of FIG. 9 are denoted by the same reference numerals, and detailed descriptions thereof are skipped.

In a light source device 1 of FIG. 10, in addition to a semiconductor laser (first semiconductor laser) 7, a second semiconductor laser 26 is disposed to emit laser light with a second wavelength different from a first wavelength of laser light emitted from the first semiconductor laser 7. Further, a third lens 27 is disposed to turn the laser light from the second semiconductor laser 26 into parallel light. At an intersecting position of the optical axis of the first semiconductor laser 7 and the optical axis of the second semiconductor laser 26, a dichroic mirror 28 is disposed to transmit the laser light with the first wavelength and to reflect the laser light with the second wavelength.

Further, as the sample 6, a sample in which at least two kinds of microparticles are mixed and which is labeled with a first fluorescent reagent and a second fluorescent reagent is used. Here, for example, the first fluorescent reagent is a specific fluorescent reagent that bonds to microparticles of only one of the kinds and that is excited by the laser light with the first wavelength. The second fluorescent reagent is a specific fluorescent reagent, different from the first fluorescent reagent, that bonds to microparticles of only the other kind of microparticles and that is excited by the laser light with the second wavelength.

In the above-described configuration, the sample 6 in which two kinds of microparticles are mixed, as described above, is set on the glass stage 5. First, the first semiconductor laser 7 is driven. Then, similarly to the second embodiment, excitation light with the first wavelength emitted from the first semiconductor laser 7 is reflected by a prism 11, is collected by a convex lens part 2a of an objective lens 2, and is collected at one point on a lower surface of the sample 6. In a portion of the lower surface of the sample 6 irradiated with the excitation light, forward scattered light 23, of first fluorescence isotropically emitted by excitation of the microparticles labeled with the first fluorescent reagent, is detected by the second detector 22. Signals detected by the second detector 22 are subjected to AD conversion, and are sent to the PC or the like. On the basis of a fluorescent image thus obtained, the microparticles of the one kind and the positions of the microparticles in the sample 6 are detected.

At the same time, similarly to the first embodiment, backward scattered light incident on the objective lens 2, of the first fluorescence isotropically emitted from the portion of the lower surface of the sample 6 irradiated with the excitation light, is detected by the first detector 15. Signals detected by the first detector 15 are subjected to AD conversion, and are sent to the PC or the like. On the basis of a fluorescent image thus obtained, the particle diameter of the microparticles of the one kind in the sample 6 is detected.

Next, the second semiconductor laser 26 is driven. Then, excitation light with the second wavelength emitted from the second semiconductor laser 26 is reflected by the dichroic mirror 28, and reaches the prism 11. Subsequently, the other kind of the microparticles in the sample 6 and the positions of the microparticles are detected by forward scattered light of the second fluorescence in the above-described manner. Further, the particle diameter of the microparticles of the other kind in the sample 6 is detected by backward scattered light of the second fluorescence.

In this case, the distance of the second sampling interval in the second scanning direction (short scanning direction) is set at a length that can obtain the minimum required resolution, and the distance of the first sampling interval in the first scanning direction (long scanning direction) is set to be shorter than the distance of the second sampling interval. Further, the spot size of the excitation light that irradiates the lower surface of the sample 6 is set so that the length in the second scanning direction is longer than the length in the first scanning direction. Therefore, it is possible to increase the detection speed of the scattered light from the microparticles during scanning in both of the directions and to increase the detection accuracy.

That is, according to this embodiment, it is possible to simultaneously, quickly, and accurately obtain the kind, position, and particle diameter of the microparticles in the sample 6.

While the microparticles in the sample 6 are sorted into two kinds of microparticles in this embodiment, this also applies to a case in which the microparticles are sorted into three or more kinds.

Fourth Embodiment

In the above-described embodiments, the rectangular glass stage 5 is scanned in two-dimensional directions, that is, the first scanning direction (long scanning direction) and the second scanning direction (short scanning direction).

In contrast, in this embodiment, a sample shaped like a wide doughnut or a wide arc is used, and a glass stage is circularly shaped to be rotatable. Moreover, an optical module is configured to move in a direction orthogonal to the rotating direction. The circumferential direction of the sample in which the scan distance in one scanning operation is long serves as the first scanning direction (long scanning direction), and the radial direction of the sample in which the scan distance in one scanning operation is short serves as the second scanning direction (short scanning direction).

Figure 11:
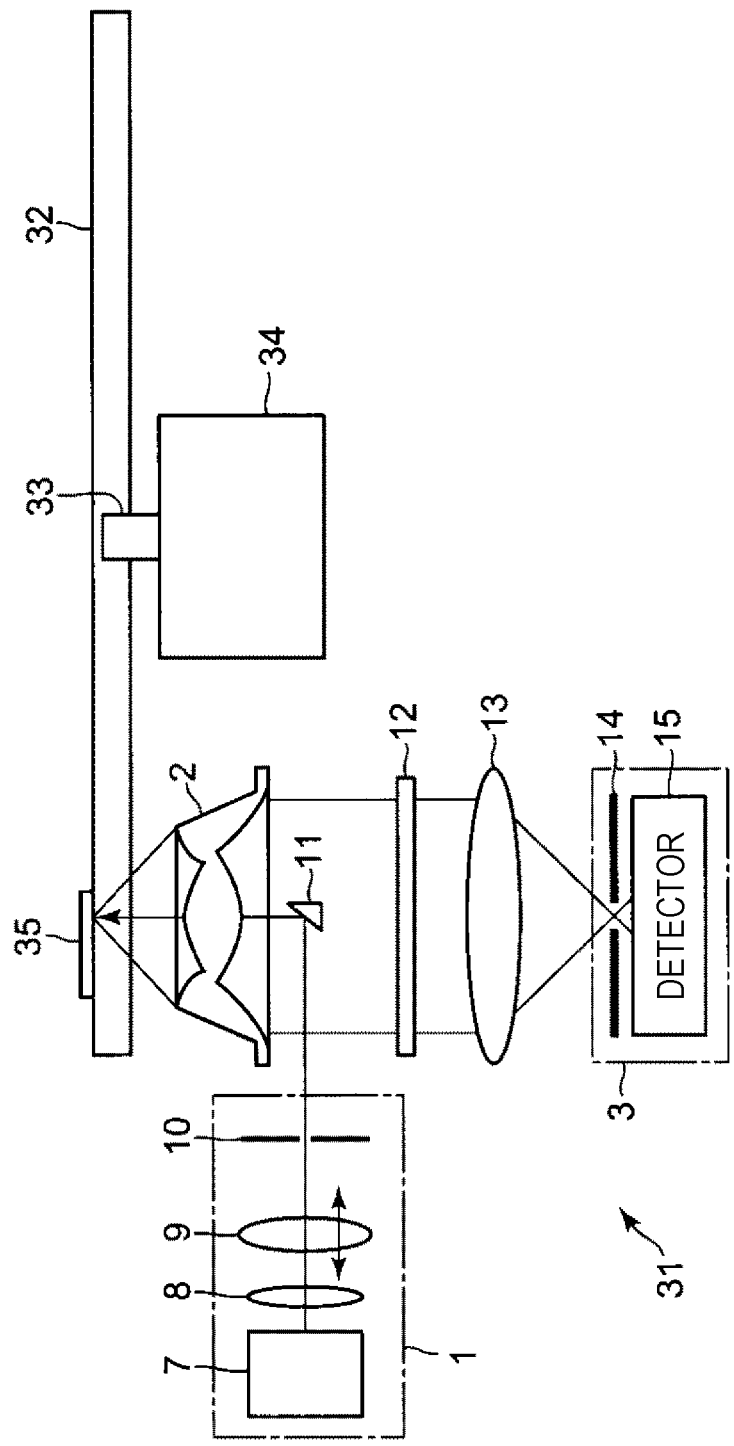
FIG. 11 illustrates schematic structures of a glass stage and an optical module different from those of FIGS. 2, 9, and 10.

FIG. 11 illustrates the schematic configuration of a glass stage and an optical module in a photodetection device according to this embodiment. An optical module 31 illustrated in FIG. 11 has a configuration substantially equal to that of the optical module 4 of the first embodiment illustrated in FIG. 2. The same members as those adopted in the optical module 4 of FIG. 2 are denoted by the same reference numerals, and detailed descriptions thereof are skipped.

In FIG. 11, a glass stage 32 is circular, and a center shaft 33 can be rotated by a spindle motor 34. In contrast, the optical module 31 is movable in a stepwise manner in the radial direction of the disc formed by the glass stage 32. The moving method for the optical module 31 is not particularly limited. For example, a frame of the optical module 31 is structured to be moved along a guide rail disposed in the radial direction by a timing belt that is caused by a stepping motor to reciprocate in the radial direction.

While the shape of the glass stage 32 is circular in this embodiment, it is not always limited to the circular shape. The shape may be any shape that allows rotation without trouble.

As described above, a sample 35 is shaped like a disc, a doughnut, or an arc. The circumferential direction serves as the first scanning direction (long scanning direction), and the radial direction of the sample serves as the second scanning direction (short scanning direction). That is, the optical module 31 is set to move by one step every time the glass stage 32 makes one rotation. However, to perform the above-described operation for the disc-shaped or doughnut-shaped sample 35 while continuously rotating the glass stage 32, it is necessary to set, on the glass stage 32, a belt-shaped non-detection area having a fixed width and extending in the radial direction and to move the optical module 31 by one step during movement of the spot of excitation light from the objective lens 2 through the non-detection area. Further, when there are a plurality of arc-shaped samples 35, it is only necessary that the optical module 31 should be moved by one step during movement of the spot of the excitation light from the objective lens 2 between the sample and the sample.

As long as there is no trouble when an obtained fluorescent image is analyzed, scanning may be spirally performed by continuously moving the optical module 31 while continuously rotating the glass stage 32.

In this embodiment, similarly to the above-described first to third embodiments, the distance of the second sampling interval in the second scanning direction (short scanning direction→radial direction) is set at a length that can obtain the minimum required resolution, and the distance of the first sampling interval in the first scanning direction (long scanning direction→circumferential direction) is set to be shorter than the distance of the second sampling interval. Further, the spot size of the excitation light that irradiates the lower surface of the sample 35 is set so that the length in the second scanning direction, that is, in the radial direction is longer than the length in the first scanning direction, that is, in the circumferential direction. Therefore, it is possible to increase the detection speed of scattered light from the microparticles during scanning in both of the directions and to increase the detection accuracy.

In this way, in this embodiment, when the planar transparent stage is two-dimensionally scanned, scanning in one direction is performed by the rotational operation, and two scanning driving operations are separately performed for the glass stage 32 and the optical module 31. Therefore, compared with the case in which two scanning driving operations are performed for only the glass stage 32 or the optical module 31, it is only necessary to arrange driving mechanisms for a disc and a pickup in a CD (compact disc) player. This achieves simplification.

In this embodiment, similarly to the above-described third embodiment, it is possible to provide a detector for detecting the forward scattered light so that a position map of microparticles in the sample 35 can be detected on the basis of the forward scattered light. In addition, it is possible to provide light sources with a plurality of wavelengths and the dichroic mirror so that the kind of the microparticles in the sample 35 can be detected.

While the semiconductor laser is used as the light source in the above-described embodiments, a compact and inexpensive LED (light emitting diode) may be used. In this case, the photodetection device can be configured at low cost.

In the third embodiment and the fourth embodiment described above, when the kind, position, and particle diameter of microparticles in the sample are detected using the forward scattered light and the backward scattered light, the forward scattered light and the backward scattered light are separately detected from florescence isotropically scattered around from the portion on the lower surface of the sample 6, 35 where excitation light emitted from the single first semiconductor laser 7 is collected.

However, the present invention is not limited thereto, and a second light source for detecting the kind and position of microparticles may be provided on a side of the sample 6, 35 opposite from the optical module 4, 31, independently of the first light source (first semiconductor laser 7) for detecting the particle diameter of the microparticles. In this case, light received by the detector for detecting the kind and position is not limited to the above-describe forward scattered light from the second light source, and may be totally reflected light or diffused reflected light. It is only necessary that the light can detect the kind and position of the microparticles with high accuracy.

An LED may be used as the second light source.

As described above, the photodetection device of the present invention includes:

a light-transmitting transparent stage 5, 32 on which a detection object 6, 35 is placed;

an excitation optical system that irradiates the detection object 6, 35 with excitation light emitted from the light source 7, 26;

a detection optical system that detects light emitted from a detection surface of the detection object 6, 35 placed on the transparent stage 5, 32 by irradiation with the excitation light;

a data sampling unit included in the detection optical system to sample an intensity of the detected light at a predetermined set interval; and an optical module 4, 21, 25, 31 that includes the light source 7, 26, the excitation optical system, and the detection optical system and that two-dimensionally and relatively scans the transparent stage 5, 32 in a first sampling direction of the data sampling unit and a second sampling direction intersecting the first sampling direction, wherein a scan length in the first sampling direction of the optical module 4, 21, 25, 31 is longer than a scan length in the second sampling direction, wherein the data sampling unit performs the sampling at a first sampling interval when the optical module 4, 21, 25, 31 performs scanning in the first sampling direction, and performs the sampling at a second sampling interval different from the first sampling interval when the optical module 4, 21, 25, 31 performs scanning in the second sampling direction, wherein the excitation optical system includes an aperture 10 that sets a spot shape of the excitation light to irradiate the detection object 6, 35, wherein a distance of the first sampling interval is set to be shorter than a distance of the second sampling interval, and wherein a shape of a spot 20a of the excitation light is set by the aperture 10 so that a spot size in the first sampling direction is smaller than a spot size in the second sampling direction.

When the planar transparent stage 5, 32 is two-dimensionally scanned, it is scanned in a short scanning direction and a long scanning direction. In the long scanning direction of these directions, since a scan distance of one scanning operation is long, scanning is easily and continuously performed at high speed for the long distance at a short sampling interval. In contrast, since the scan distance of one scanning operation is short in the short scanning direction, the above-described high-speed scanning is difficult.

According to the above configuration, the first sampling direction serves as the long scanning direction, and the second sampling direction serves as the short scanning direction. The distance of the first sampling interval in the first scanning direction that can be decreased because the first sampling direction is the long scanning direction is set to be shorter than the distance of the second sampling interval in the second sampling direction that cannot be decreased because the second sampling direction is the short scanning direction. This allows sampling to obtain the detection light intensity at high speed and with high accuracy as a whole.

Further, the shape of the spot 20a of the excitation light from the light source 7, 26 on the detection object 6, 35 is set so that the spot size in the first sampling direction is smaller than the spot size in the second sampling direction. That is, the size is set to be small in the direction in which the sampling interval is short and to be large in the direction in which the sampling interval is long. Therefore, it is possible to reduce the increase of skipping of light from the microparticles and the like emitted from the detection surface of the detection object 6, 35 owing to the inability to shorten the distance of the second sampling interval in the second sampling direction serving as the short scanning direction, and to further increase the detection accuracy.

That is, according to the present invention, it is possible to increase the detection speed for light emitted from the detection surface of the detection object 6, 35 during scanning in both of the directions and to increase the detection accuracy.

In the photodetection device according to an embodiment:

a ratio of the distance of the second sampling interval to the distance of the first sampling interval is two or more, and a ratio of the spot size in the second sampling direction to the spot size in the first sampling direction of the spot 20a of the excitation light is two or more.

According to this embodiment, the ratio of the distance of the second sampling interval to the distance of the first sampling interval is two or more, and the ratio of the size in the second sampling direction to the size in the first sampling direction of the spot 20a of the excitation light is two or more. In this way, the effects of increasing the detection speed and increasing the detection accuracy can be clearly obtained when light emitted from the detection surface of the detection object 6, 35 is detected.

In the photodetection device according to an embodiment, microparticles 17 that emit light by irradiation with the excitation light are two-dimensionally dispersed in the detection object 6, 35, a size of the microparticles 17 is smaller than the spot size in the first sampling direction of the spot 20a of the excitation light formed on the detection object 6, 35, and the detection optical system detects the microparticles 17 dispersed in the detection object 6, 35 by detecting the light emitted from the microparticles 17.

According to this embodiment, when the microparticles 17 dispersed in the detection object 6, 35 are detected, since the size of the microparticles 17 is smaller than the size in the first sampling direction of the spot 20a of the excitation light, it is possible to prevent the microparticle 17 from being skipped during scanning in the first sampling direction and to achieve high detection accuracy.

The photodetection device according to an embodiment includes:

a first operating unit that causes the optical module 4, 21, 25 to reciprocate relative to the transparent stage 5 in the first sampling direction; and a second operating unit that causes the optical module 4, 21, 25 to reciprocate relative to the transparent stage 5 in the second sampling direction substantially orthogonal to the first sampling direction.

According to this embodiment, in the photodetection device in which the optical module 4, 21, 25 or the transparent stage 5 is relatively scanned in two sampling directions that are substantially orthogonal to each other, it is possible to increase the detection speed for light emitted from the detection surface of the detection object 6 during scanning in both of the sampling directions and to increase the detection accuracy.

In the photodetection device according to an embodiment, the first sampling direction is a direction of a circumference, and the second sampling direction is a radial direction of the circumference, the photodetection device further includes a first operating unit that causes the transparent stage 32 to rotate on a center of the circumference relative to the optical module 31, and a second operating unit that causes the optical module 31 to reciprocate in the second sampling direction relative to the transparent stage 32.

According to this embodiment, scanning in one direction is performed by the rotating operation when the planar transparent stage 32 is two-dimensionally scanned, and two scanning driving operations in both of the one direction and the other direction are separately performed for the transparent stage 32 and the optical module 31. Therefore, the structure of the operating units for scanning driving can be simplified, compared with the case in which two scanning driving operations are conducted on only the transparent stage 32 or the optical module 31.

REFERENCE SIGNS LIST

1 light source device
2 objective lens
3 detection device
4, 21, 25, 31 optical module
5, 32 glass stage
6, 35 sample
7 semiconductor laser (first semiconductor laser)
8 first lens
9 spot-size adjusting lens
10 aperture
11 prism
12 ND filter
13 second lens
14 pinhole
15 detector (first detector)
16 rotating folder
17 microparticle
19 curve showing analog data
20a spot of excitation light formed using aperture
20b spot of excitation light formed without using aperture
22 second detector
23 forward scattered light
26 second semiconductor laser
27 third lens
28 dichroic mirror
33 center shaft of glass stage
34 spindle motor

The invention claimed is:

1. A photodetection device comprising:
a light-transmitting transparent stage on which a detection object is placed;
an excitation optical system that irradiates the detection object with excitation light emitted from a light source in a direction perpendicular to the transparent stage;
a detection optical system that detects light emitted from a detection surface of the detection object placed on the transparent stage by irradiation with the excitation light;
a data sampling circuit included in the detection optical system to sample an intensity of the detected light at a predetermined set interval; and
an optical module that includes the light source, the excitation optical system, and the detection optical system and that two-dimensionally and relatively scans the transparent stage in a first sampling direction of the data sampling circuit and a second sampling direction intersecting the first sampling direction, wherein
a scan length in the first sampling direction in the optical module is longer than a scan length in the second sampling direction,
the data sampling circuit performs the sampling at a first sampling interval when the optical module performs scanning in the first sampling direction, and performs the sampling at a second sampling interval different from the first sampling interval when the optical module performs scanning in the second sampling direction,
the excitation optical system includes an aperture that defines a spot shape of the excitation light to irradiate the detection object,
a distance of the first sampling interval is shorter than a distance of the second sampling interval, and
a spot size of the excitation light in the first sampling direction is smaller than a spot size in the second sampling direction.

2. The photodetection device according to claim 1,
wherein a ratio of a distance of the second sampling interval to a distance of the first sampling interval is two or more, and
wherein a ratio of the spot size in the second sampling direction to the spot size in the first sampling direction is two or more.

3. The photodetection device according to claim 1,
wherein microparticles that emit light after irradiation by the excitation light are two-dimensionally dispersed in the detection object,
wherein a size of the microparticles is smaller than the spot size irradiated on the detection object in the first sampling direction, and
wherein the detection optical system detects the microparticles dispersed in the detection object by detecting the light emitted from the microparticles.

4. The photodetection device according to claim 1, further comprising:
a first operator that causes the optical module to reciprocate relative to the transparent stage in the first sampling direction, and
a second operator that causes the optical module to reciprocate relative to the transparent stage in the second sampling direction substantially orthogonal to the first sampling direction.

5. The photodetection device according to claim 1,
wherein the first sampling direction is a direction of a circumference, and the second sampling direction is a radial direction of the circumference, and
wherein the photodetection device further includes:
a first operator that causes the transparent stage to rotate on a center of the circumference relative to the optical module; and a second operator that causes the optical module to reciprocate relative to the transparent stage in the second sampling direction.

\* \* \* \* \*